United States Patent [19]
Landis et al.

[11] Patent Number: 5,780,397
[45] Date of Patent: Jul. 14, 1998

[54] EXTREME PRESSURE ADDITIVE

[75] Inventors: Phillip S. Landis, Alexandria, Va.; Blaine N. Rhodes, Vancouver; Will F. Williamson, Seattle, both of Wash.

[73] Assignee: International Lubricants, Inc., Seattle, Wash.

[21] Appl. No.: 719,355

[22] Filed: Sep. 25, 1996

[51] Int. Cl.$^6$ .................................................. C10M 129/68
[52] U.S. Cl. ........................ 508/346; 508/351; 508/352; 554/78; 554/85
[58] Field of Search .............................. 508/346, 351, 508/352, 491; 554/78, 85

[56] References Cited

U.S. PATENT DOCUMENTS

| | | | |
|---|---|---|---|
| 2,142,998 | 1/1939 | Chittick | 508/352 |
| 2,357,346 | 9/1944 | Musselman | 508/352 |
| 2,375,061 | 5/1945 | Williams | 508/352 |
| 2,385,832 | 10/1945 | Musselman | 508/351 |
| 2,399,243 | 4/1946 | Musselman | 508/351 |
| 2,422,206 | 6/1947 | Musselman | 508/352 |
| 2,480,873 | 9/1949 | Musselman | 508/352 |
| 3,288,819 | 11/1966 | Tichelaar et al. | 554/75 |
| 5,229,023 | 7/1993 | Landis | 508/465 |

*Primary Examiner*—Alan Diamond
*Assistant Examiner*—Cephia D. Toomer
*Attorney, Agent, or Firm*—Jeffrey B. Oster

[57] ABSTRACT

There is disclosed a lubricant additive ingredient that imparts extreme pressure anti-wear properties to lubricant additive compositions. Specifically, there is disclosed a derivative of a vegetable oil triglyceride, a wax ester or a telomerized oil reacted with phosphorous pentasulfide to produce a phosphorous-sulfur (PS) extreme pressure additive.

6 Claims, 3 Drawing Sheets

5,780,397

1

EXTREME PRESSURE ADDITIVE

TECHNICAL FIELD OF THE INVENTION

The present invention provides a lubricant additive ingredient that imparts extreme pressure anti-wear properties to lubricant additive compositions. Specifically, the present invention provides a derivative of a base oil reacted with phosphorous and sulfur-containing material to produce a phosphorous-sulfur (PS) extreme pressure additive.

BACKGROUND OF THE INVENTION

The field of lubricant additives has seen a wide variety of materials used to reduce friction and wear between moving parts. Lubricants are composed principally of a base stock and lubricant additives. The lubricant additive provides the anti-friction and anti-wear characteristics to the lubricant. The base stock imparts improved viscosity and thermal oxidative stability, which can also be improved by the addition of various additives. One significant advance in the field was the invention of a material called a "telomer". The telomer invention is described in WO92/07051 and in U.S. Pat. No. 5,229,023, the disclosures of which are incorporated by reference herein.

Briefly, a telomer is a polymerized triglyceride oil, principally derived from a seed oil, that has thermal oxidative stability and viscosity improvement characteristics that makes the telomer an essential component of a large variety of lubricant compositions. The process to synthesize telomers begins with a triglyceride and heats the oil in a non-oxidizing atmosphere with a trace water catalyst to lower the iodine number such that no more than 4% of the fatty acid chains of the telomerized vegetable oil are polyunsaturated. The triglyceride vegetable oils are characterized as having from about 10% to about 75% polyunsaturated fatty acid chains of from about 16 to about 26 carbon atoms in length.

The present invention was made in an effort to improve the telomer product and other appropriate base oils by discovering a phosphorous sulfur "PS" derivative having the desirable viscosity and oxidative stability properties as a telomer and the anti-wear properties of an extreme-pressure additive.

SUMMARY OF THE INVENTION

The present invention provides an extreme pressure additive composition comprising the reaction product of a base oil with from about 0.01% to about 10.0% by weight of a phosphorus/sulfur compound under anaerobic conditions at temperatures from about 150° C. to about 250° C. for at least two hours but no longer than 48 hours, wherein the base oil is selected from the group consisting of triglyceride oils having at least a monounsaturated alkyl chain (branched or straight), wax esters having from about 6 to about 22 carbon atom chains (branched or straight) on either side of the ester group and containing at least one carbon-carbon double bond, and telomer oils having at least one carbon-carbon double bond in each triglyceride monomer in an aliphatic ring structure, and wherein the phosphorus/sulfur compound is selected from the group consisting of phosphorous pentasulfide ($P_2S_5$) and its dimer $P_4S_{10}$, $P_4S_3$, $P_4S_5$ and $P_4S_7$. Preferably, the reaction product of the phosphorous pentasulfide reaction contains an amount of sulfur equal to about 2.5 times the weight percent of phosphorous. Preferably, a second reaction step adds from about 0.1% to about 20.0% by weight of a dialkyl hydrogen phosphite or a monoalkyl hydrogen phosphite to increase the phosphorous content of the resulting reaction product to improve anti-friction characteristics, wherein the alkyl moiety of dialkyl hydrogen phosphite or monoalkyl hydrogen phosphite is independently selected from a saturated straight chain alkyl group having from two to 20 carbon atoms in length.

The present invention further provides a process for synthesizing an extreme pressure PS additive composition, comprising reacting a base oil with from about 0.01% to about 10.0% by weight of a phosphorous/sulfur compound under anaerobic conditions at temperatures from about 150° C. to about 250° C. for at least two hours but no longer than 48 hours, wherein the base oil is selected from the group consisting of triglyceride oils having at least a monounsaturated alkyl chain (branched or straight), wax esters having from about 6 to about 22 carbon atom chains (branched or straight) on either side of the ester group and containing at least one carbon-carbon double bond, and telomer oils having at least one carbon-carbon double bond in each triglyceride monomer in an aliphatic ring structure, and wherein the phosphorus/sulfur compound is selected from the group consisting of phosphorous pentasulfide ($P_2S_5$) and its dimer $P_4S_{10}$, $P_4S_3$, $P_4S_5$ and $P_4S_7$. Preferably, the reaction product of the phosphorous pentasulfide reaction contains an amount of sulfur equal to about 2.5 times the weight percent of phosphorous. Preferably, a second reaction step adds from about 0.1% to about 20.0% by weight of a dialkyl hydrogen phosphite or a monoalkyl hydrogen phosphite to increase the phosphorous content of the resulting reaction product to improve anti-friction characteristics, wherein the alkyl moiety of dialkyl hydrogen phosphite or monoalkyl hydrogen phosphite is independently selected from a saturated straight or branched chain alkyl group having from two to 20 carbon atoms.

BRIEF DESCRIPTION OF THE DRAWINGS

FIG. 2 shows high absorption in the 900–1100 $cm^{-1}$ range showing the presence of phosphorous-sulfur bonds. The absorption at 1050 $cm^{-1}$ indicates carbon-sulfur-phosphorous bonds, confirming a chemical reaction between the telomer and $P_2S_5$.

FIG. 3 shows a larger 1050 $cm^{-1}$ absorption, indicating dibutyl ester carbon-oxygen-phosphorous bonds and a lack of double bonds at 3005 $cm^{-1}$ indicating that the dibutyl hydrogen phosphite adducted to the remaining double bonds in the telomer base oil.

DETAILED DESCRIPTION OF THE INVENTION

Figure 1:
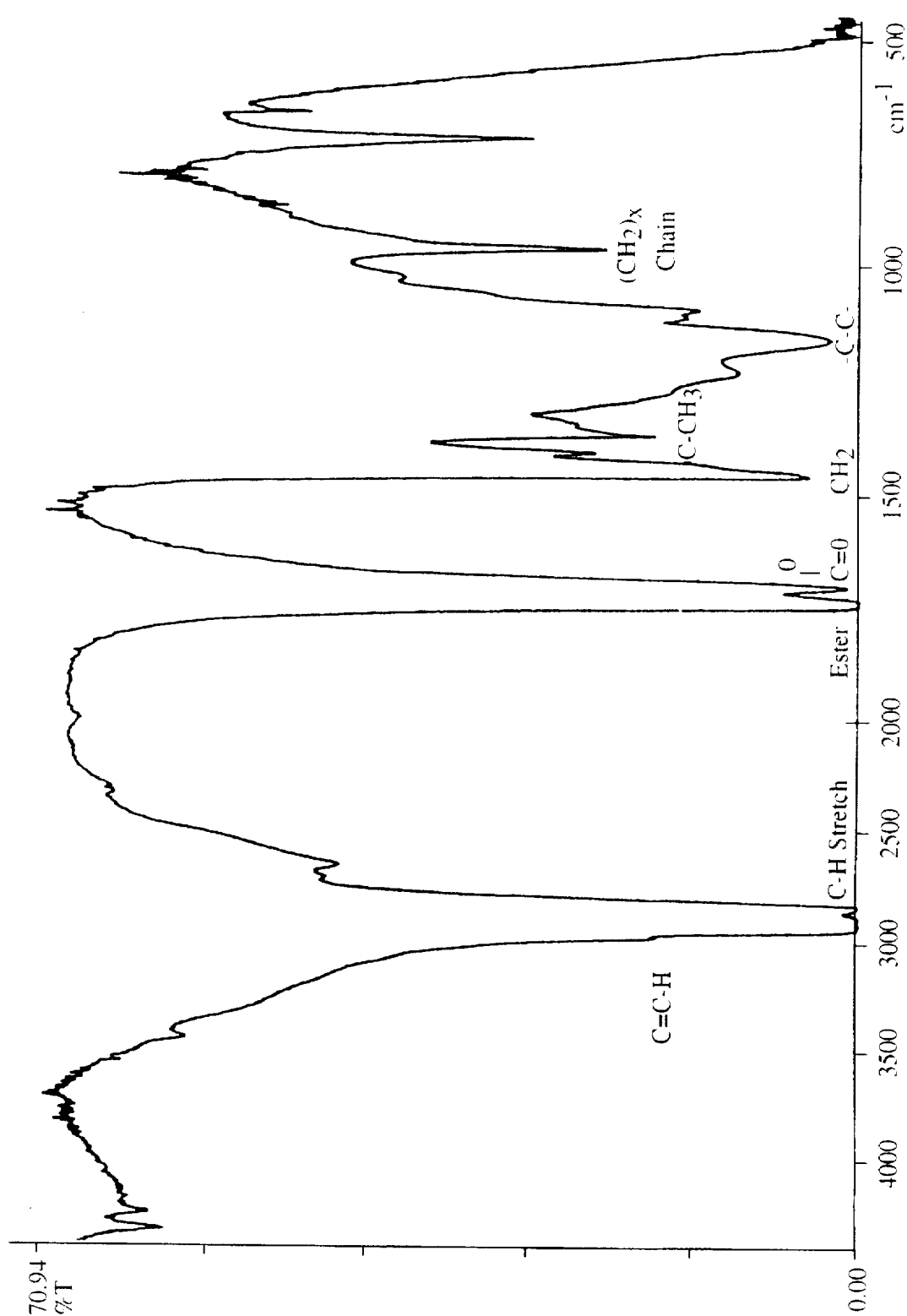
FIG. 1 shows a control infrared (IR) scan of a 6000 sus telomer product made from 60% HEAR oil and 40% linseed oil (both by weight). This figure is a control scan that is used for comparison to scans of the inventive compounds.

The present invention provides an extreme pressure additive composition comprising the reaction product of a base oil with from about 0.01% to about 10.0% by weight phosphorous pentasulfide ($P_2S_5$) under anaerobic conditions at temperatures from about 150° C. to about 250° C. for at least two hours but no longer than 48 hours, wherein the base oil is selected from the group consisting of triglyceride oils having at least a monounsaturated alkyl chain (branched or straight), wax esters having from about 6 to about 22 carbon atom chains (branched or straight) on either side of the ester group and containing at least one carbon-carbon double bond, and telomer oils having at least one carbon-carbon double bond in each triglyceride monomer in an aliphatic ring structure. Preferably, the reaction product of the phosphorous pentasulfide reaction contains an amount of sulfur equal to about 2.5 times the amount of phosphorous by weight.

$P_2S_5$ reacts with remaining unsaturated (carbon-carbon double bonds) on the telomer oil, triglyceride or wax ester, linking a phosphorous group with the site of unsaturation and allowing sulfur to cross link with other chains or with other $P_2S_5$ molecules. When analyzed for elemental phosphorous, the final product of this reaction contains between 0.1% and 20.0% phosphorous by weight. When $P_2S_5$ is used, the amount of sulfur on the final product is in stoichiometric proportion to the amount of phosphorous. Specifically, for $P_2S_5$ addition, the weight percent of sulfur is equal to 2.58 times the weight percent of phosphorous.

From a structural standpoint, the initial $P_2S_5$ reaction will be $P_4S_{10}$ (dimer of $P_2S_5$) reacting with a carbon-carbon double bond of the base oil, shown structurally as:

wherein x and y are integers denoting the alkyl chain length (straight or branched) and R denotes the rest of the base oil molecule. This forms an initial reaction product with the addition of phosphorous and sulfur as follows:

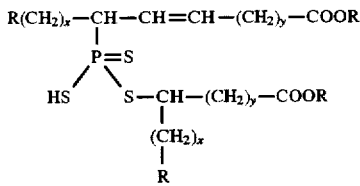

This product can also be made into its phosphite adduct derivative by the second step addition of an alkyl (straight or branched) phosphorous derivative, such as

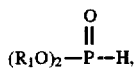

wherein R1 is a straight or branched alkyl group having from 2 to 20 carbon atoms. The phosphite adduct gets added across the carbon-carbon double bond to form a product as follows:

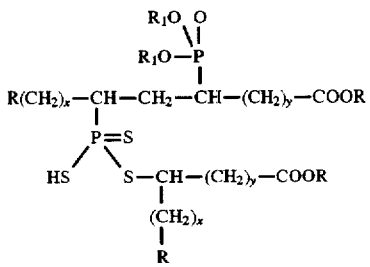

wherein x, y, R and $R_1$ are defined as above.

The EP product is formed by a reaction of a base oil with a compound containing phosphorous and sulfur exclusively or phosphorous, sulfur and oxygen exclusively in stoichiometric ratios of 1%–50%, 3%–75%, and 0%–50% by weight respectively under anaerobic conditions at temperatures within the range of 150° C. to 250° C. for at least four hours. Preferably, the base oil is an unsaturated triglyceride, such as rapeseed oil (HEAR) or linseed oil or combinations thereof, and the preferred reactant is phosphorous pentasulfide.

Preferably, a second reaction step adds from about 0.1% to about 20.0% by weight of a dialkyl hydrogen phosphite or a monoalkyl hydrogen phosphite to increase the phosphorous content of the resulting reaction product to improve anti-friction characteristics, wherein the alkyl moiety of dialkyl hydrogen phosphite or monoalkyl hydrogen phosphite is independently selected from a saturated straight or branched chain alkyl group having from two to 20 carbon atoms.

The present invention further provides a process for synthesizing an extreme pressure additive composition comprising reacting a base oil with from about 0.01% to about 10.0% by weight phosphorous pentasulfide ($P_2S_5$) under anaerobic conditions at temperatures from about 150° C. to about 250° C. for at least two hours but no longer than 48 hours, wherein the base oil is selected from the group consisting of triglyceride oils having at least a monounsaturated alkyl chain, wax esters having from about 6 to about 22 carbon atom chains on either side of the ester group and containing at least one carbon-carbon double bond, and telomer oils having at least one carbon-carbon double bond in each triglyceride monomer in an aliphatic ring structure. Preferably, the reaction product of the phosphorous pentasulfide reaction contains an amount of sulfur equal to about 2.5 times the amount of phosphorous by weight. Preferably, a second reaction step adds from about 0.1% to about 20.0% by weight of a dialkyl hydrogen phosphite or a monoalkyl hydrogen phosphite to increase the phosphorous content of the resulting reaction product to improve anti-friction characteristics, wherein the alkyl moiety of dialkyl hydrogen phosphite or monoalkyl hydrogen phosphite is independently selected from a saturated straight or branched chain alkyl group having from two to 20 carbon atoms.

EXAMPLE 1

This example illustrates the synthesis of an inventive EP additive using a mixture of rapeseed oil (HEAR) and linseed oil, both unsaturated triglyceride oils, as the base oil and phosphorous pentasulfide as the PS reactant. Approximately 500 g of a mixture of HEAR and linseed oil in a ratio of 60% HEAR oil to 40% linseed oil by weight into a reactor that was heated to 150° C. Phosphorous pentasulfide (17.9 g) was slowly fed into the reactor over four hours of time. This was the equivalent of a 1% by weight on a phosphorous basis of $P_2S_5$. It was important not to raise the temperature much above 150° C. as this will cause the formation of poly-sulfide chains causing the product to increase viscosity and degrade thermal stability of the product. Phosphorous pentasulfide was fed continuously as the solids were observed to dissolve. After the reactants are added, the temperature of the reaction mixture was raised to 200° C. over a minimum time of 30 minutes and the reaction continued for 2 hours. The product was cooled under nitrogen gas at about 100° C., after which air exposure was allowed and the product was evaluated and analyzed.

Figure 2:
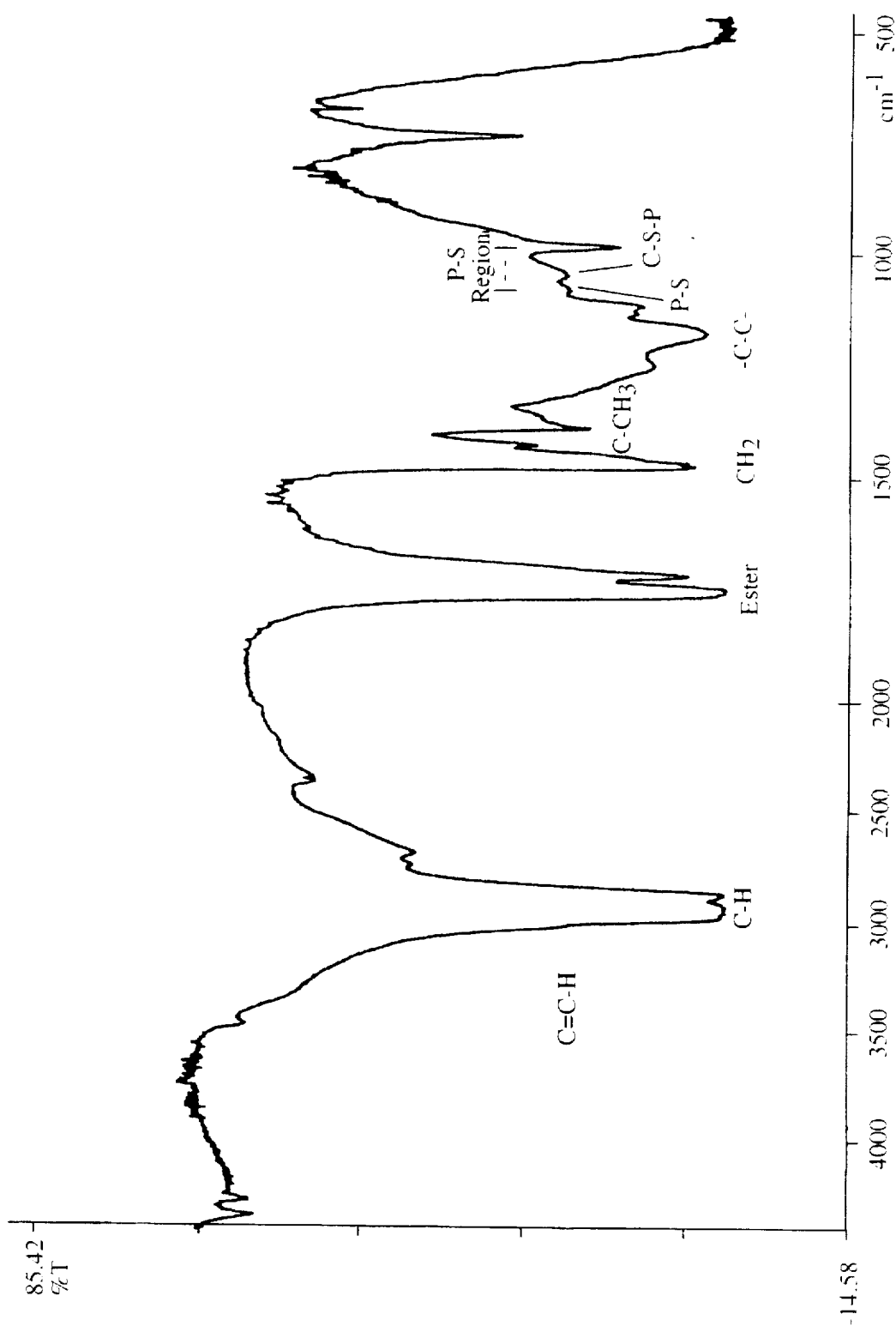
FIG. 2 shows an IR scan of the product from example 1. This product is the reaction of a 6000 sus telomer with 1% (by weight on a phosphorous basis) of $P_2S_5$. When compared with FIG. 1.

The products were subject to IR scans to determine the presence of new bond formations. FIG. 1 (Scan D) is a control IR scan of a 6000 sus telomer product formed by the same ratio of HEAR oil and linseed oil as provided in this example. FIG. 2 (scan A) shows the product of this example and should be compared with the control FIG. 1. FIG. 2 shows high absorption in the 900–1100 cm$^{-1}$ range, showing the presence of phosphorous-sulfur bonds. The absorption at 1050 cm$^{-1}$ indicates carbon-sulfur-phosphorous bonds and confirming the chemical reaction between the telomer and $P_2S_5$ or $P_4S_{10}$.

EXAMPLE 2

This example illustrates a synthesis of a preferred EP additive. The product from example 1 is further reacted with a dialkyl (butyl) hydrogen phosphite. Specifically, The product of example 1 is cooled down to only 150° C. and a charge of 2.7% (by weight) dibutyl hydrogen phosphite and 1% (by weight) di-tertiary butyl peroxide catalyst was added to the reactor over a five minute period. The product was maintained over heat and a nitrogen gas blanket for 3–5 hours, or until completion of the phosphite reaction had consumed the phosphite (as evidenced by condensation of butyl alcohol overhead. When the reaction was completed, nitrogen is discontinued and the product was cooled to about 100° C. under a vacuum for discharge from the reaction vessel.

Figure 3:
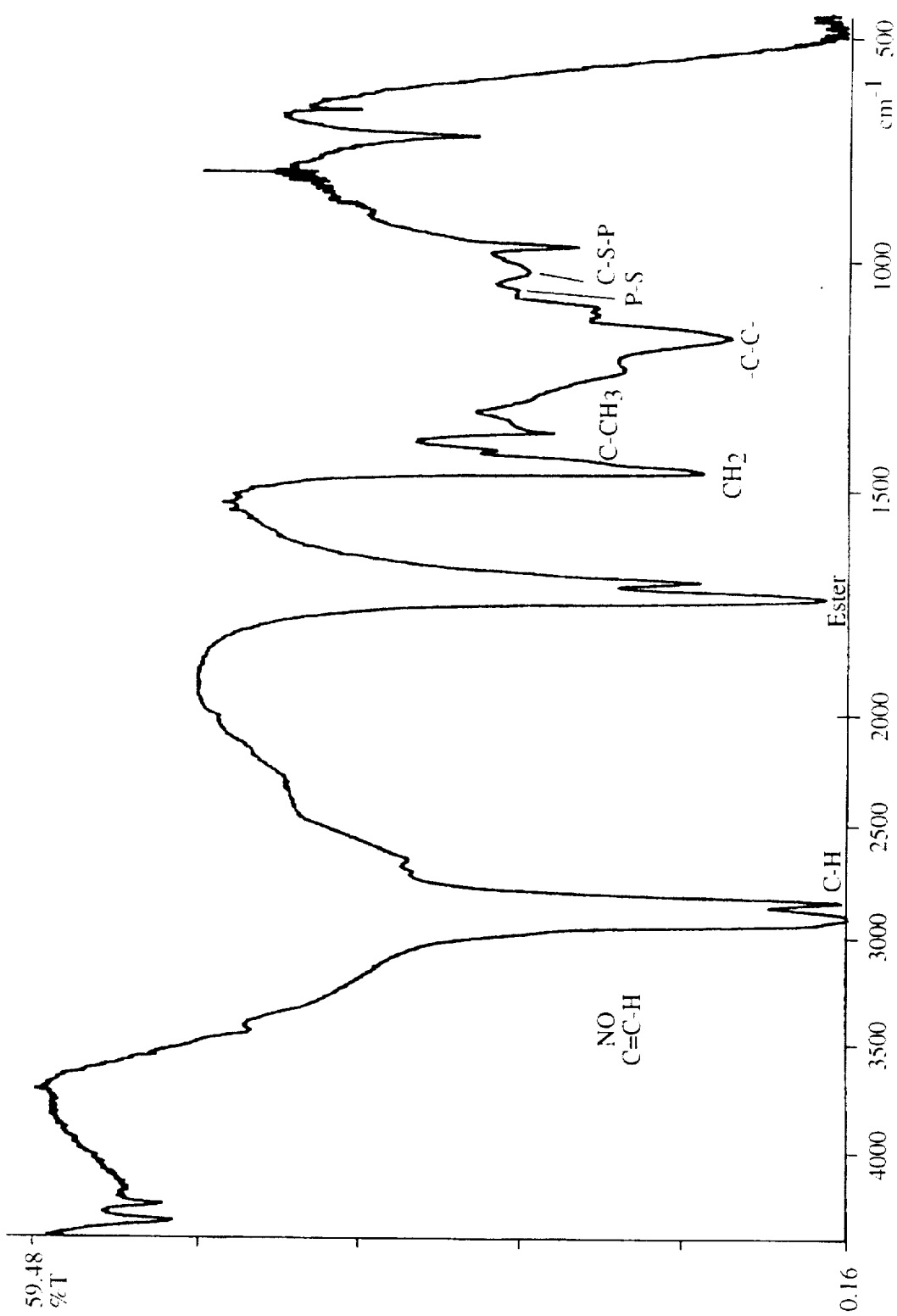
FIG. 3 shows an IR scan of the product from example 2, that is the product from example 1 (FIG. 2) further reacted with dibutyl hydrogen phosphite. When compared with the IR scan of FIG. 2.

FIG. 3 (scan B) shows an IR scan of the product of example 2. When compared with FIG. 2, the scan for the product of example 2 (FIG. 3) shows a larger 1050 cm$^{-1}$ absorption, indicating dibutyl ester carbon-oxygen-phosphorous bonds and a lack of double bonds at 3005 cm$^{-1}$, which indicates that the dibutyl hydrogen phosphite adducted to the remaining double bonds of the telomer base oil.

EXAMPLE 3

This example illustrates a comparison of various inventive EP additives with current commercial EP additives in various predictive test for anti-wear and anti-friction characteristics. A lubricity test using a 4 Ball apparatus tested compared anti-wear properties of four EP products added as 2.5% by weight into 97.5% MVI Neutral Base Oil. Product A is a commercial chlorinated paraffin EP product (Mayfree 133, Mayco Oil and Chemical, Warminster, Pa.), product B is a commercial chlorine-free EP product (Idachlor SS, Ideos, Inc., Chicago, Ill.) product C is the product of example 1 herein and product D is the product of example 2 herein. The following table 1 shows that the inventive EP additives are superior to current commercial EP additives.

TABLE 1

| Test | Units | Control | Product A | Product B | Product C | Product D |
|---|---|---|---|---|---|---|
| 4 Ball ear | wear scar dia mm | 0.70 | 0.84 | 0.58 | 0.40 | 0.43 |
| 4 Ball EP | weld load kg | <100 | 160 | 200 | 250 | 250 |

Tables 2 and 3 show a Falex pin and Vee block test comparison of products A–D and MVI vehicle control at various clamp forces. The MVI vehicle control tests failed at a load of 500 [units?]. Table 2 shows the torque measurements and table 3 shows the temperature (° C.) measurement.

TABLE 2

| clamp force | Control | Product A | Product B | Product C | Product D |
|---|---|---|---|---|---|
| 0 | 0 | 0 | 0 | 0 | 0 |
| 250 | 13 | 12 | 9 | 9 | 12 |
| 500 | fail | 27 | 13 | 16 | 18 |
| 750 | | 49 | 19 | 20 | 25 |
| 1000 | | 50 | 22 | 27 | 31 |
| 1250 | | 48 | 26 | 31 | 37 |
| 1500 | | 49 | 29 | 34 | 41 |
| 1750 | | 48 | 36 | 36 | 46 |
| 2000 | | 48 | 50 | 38 | 48 |
| 2250 | | 48 | 90 | 42 | 49 |
| 2500 | | 50 | 95 | 47 | 52 |
| 2750 | | 52 | 90 | 63 | 56 |
| 3000 | | 56 | 82 | 65 | 61 |

TABLE 3

| clamp force | Control | Product A | Product B | Product C | Product D |
|---|---|---|---|---|---|
| 0 | 120 | 120 | 120 | 120 | 120 |
| 250 | 120 | 138 | 123 | 125 | 155 |
| 500 | fail | 185 | 162 | 160 | 156 |
| 750 | | 185 | 164 | 160 | 157 |
| 1000 | | 185 | 168 | 162 | 158 |
| 1250 | | 191 | 175 | 164 | 159 |
| 1500 | | 198 | 180 | 167 | 162 |
| 1750 | | 205 | 179 | 171 | 166 |
| 2000 | | 212 | 178 | 176 | 170 |
| 2250 | | 217 | 185 | 182 | 176 |
| 2500 | | 223 | 218 | 188 | 182 |
| 2750 | | 230 | 246 | 200 | 191 |
| 3000 | | 236 | 262 | 218 | 200 |

These data (tables 2 and 3) show reduced friction, as manifest by lower temperature readings, for the inventive EP additive over existing EP additives when added at the same concentration in MVI base oil. Moreover, the lower torque numbers (Table 2) provide evidence that the inventive EP additive provides superior results over existing EP additives.

EXAMPLE 4

This example illustrates a comparison of the inventive EP additive of example 1 in gear fluid compared with a commercial EP additive in gear fluid versus control gear fluids without additives in a pin and vee block test, which is a measure of friction and wear. Table 4 shows the torque readings (in pounds) over different run times for each of the four (additive or no additive) gear fluid formulas called Products A–D. Product A is the product of example 2 as 6% by weight in an 80W90 gear fluid (low pass). Product B is a high pass gear fluid which is an ASTM standard reference oil. Product C is the low pass gear fluid. Product D is a commercial GL5 approved gear oil (Valvoline).

TABLE 4

| Falex pin and vee wear testing | Product A | Product B | Product C | Product D |
|---|---|---|---|---|
| pin wear (mg) | 126.2 mg | 101.4 mg | 219.9 mg | 193.4 mg |
| max temp. (°C.) | 200.2 | 245.8 | 230.1 | 255 |

TABLE 4-continued

| 2 hr at 1250 lb applied load | torque (lb.) | torque (lb.) | torque (lb.) | torque (lb.) |
|---|---|---|---|---|
| 250 | 9 | 9 | 11 | 9 |
| 500 | 14 | 40 | 43 | 46 |
| 750 | 22 | 39 | 45 | 58 |
| 1000 | 21 | 40 | 49 | 57 |
| 1250 | 24 | 46 | 56 | 43 |
| 1250 | 30 | 38 | 44 | 36 |
| 1250 | 33 | 34 | 42 | 32 |
| 1250 | 32 | 41 | 42 | 32 |
| 1250 | 34 | 39 | 46 | 31 |
| 1250 | 33 | 34 | 43 | 29 |
| 1250 | 32 | 33 | 42 | 30 |
| 1250 | 35 | 32 | 43 | 37 |
| 1250 | 39 | 34 | 41 | 39 |
| 1250 | 41 | 36 | 43 | 36 |
| 1250 | 40 | 38 | 41 | 38 |
| 1250 | 40 | 53 | 40 | 30 |
| 1250 | 42 | 58 | 40 | 29 |

We claim:

1. An extreme pressure additive composition comprising the reaction product of a base oil with from about 0.01% to about 10.0% by weight of a phosphorous/sulfur compound under anaerobic conditions at temperatures from about 150° C. to about 250° C. for at least two hours but no longer than 48 hours, wherein the base oil is selected from the group consisting of triglyceride oils having at least an alkenyl chain (branched or straight), wax esters having from about 6 to about 22 carbon atom chains (branched or straight) on either side of the ester group and containing at least one carbon-carbon double bond, and telomer oils characterized in having an aliphatic ring structure formed by a Diels Alder reaction having at least one carbon-carbon double bond in each triglyceride monomer in an aliphatic ring structure, and wherein the phosphorus/sulfur compound is selected from the group consisting of phosphorous pentasulfide ($P_2S_5$) and its dimer $P_4S_{10}$, $P_4S_3$, $P_4S_5$ and $P_4S_7$.

2. The extreme pressure additive composition of claim 1 wherein a second reaction step adds from about 0.1% to about 20.0% by weight of a dialkyl hydrogen phosphite or a monoalkyl hydrogen phosphite to increase the phosphorous content of the resulting reaction product, wherein the alkyl moiety of dialkyl hydrogen phosphite or monoalkyl hydrogen phosphite is independently selected from a straight or branched chain alkyl group having from two to twenty carbon atoms in length.

3. The extreme pressure additive composition of claim 1 wherein the phosphosphorous/sulfur compound is $P_2S_5$ or its dimer $P_4S_{10}$.

4. The extreme pressure additive composition of claim 2 wherein the second reaction step adds dibutyl hydrogen phosphite.

5. A process for synthesizing an extreme pressure additive composition comprising reacting a base oil with from about 0.01% to about 10.0% by weight of a phosphorous/sulfur compound under anaerobic conditions at temperatures from about 150° C. to about 250° C. for at least two hours but no longer than 48 hours, wherein the base oil is selected from the group consisting of triglyceride oils having at least an alkenyl chain (branched or straight), wax esters having from about 6 to about 22 carbon atom chains (branched or straight) on either side of the ester group and containing at least one carbon-carbon double bond, and telomer oils having at least one carbon-carbon double bond in each triglyceride monomer in an aliphatic ring structure, and wherein the phosphorus/sulfur compound is selected from the group consisting of phosphorous pentasulfide ($P_2S_5$) and its dimer $P_4S_{10}$, $P_4S_3$, $P_4S_5$ and $P_4S_7$.

6. The process for synthesizing an extreme pressure additive composition of claim 5, further comprising second reaction step adding from about 0.1% to about 20.0% by weight of a dialkyl hydrogen phosphite or a trialkyl hydrogen phosphite to increase the phosphorous content of the resulting reaction product, wherein the alkyl moiety of dialkyl hydrogen phosphite or trialkyl hydrogen phosphite is independently selected from a straight or branched chain alkyl group having from two to 20 carbon atoms in length.

* * * * *